United States Patent [19]
Arnott

[11] Patent Number: 5,269,795
[45] Date of Patent: Dec. 14, 1993

[54] TREPHINE DEVICE FOR REMOVING ANTERIOR EPITHELIAL CELLS FROM CORNEAL SURFACES

[76] Inventor: Eric J. Arnott, Trottsford Farm, Headley Near Bordon, Hampshire, England, GU35 8TF

[21] Appl. No.: 725,349
[22] Filed: Jul. 3, 1991
[51] Int. Cl.⁵ .............................................. A61B 17/32
[52] U.S. Cl. .................................... 606/166; 606/171
[58] Field of Search ............... 606/107, 166, 167, 170, 606/169, 179, 180, 171; 604/22; 128/751-755

[56] References Cited

U.S. PATENT DOCUMENTS

| | | | |
|---|---|---|---|
| 3,976,077 | 8/1976 | Kerfoot, Jr. | 606/107 |
| 3,990,453 | 11/1976 | Douvas et al. | 606/107 |
| 4,190,050 | 2/1980 | Bailey . | |
| 4,320,761 | 3/1982 | Haddad | 606/107 |
| 4,336,805 | 6/1982 | Smirmaul . | |
| 4,423,728 | 1/1984 | Lieberman . | |
| 4,744,362 | 5/1988 | Grundler . | |
| 4,750,491 | 6/1988 | Kaufman et al. . | |
| 4,763,651 | 8/1968 | Kaufman et al. . | |
| 4,782,833 | 11/1988 | Einhorn et al. . | |
| 4,796,623 | 1/1989 | Krasner et al. . | |
| 4,834,748 | 5/1989 | McDonald | 606/166 |
| 4,913,143 | 4/1990 | Oloff et al. . | |

Primary Examiner—Stephen C. Pellegrino
Assistant Examiner—Wm. Lewis
Attorney, Agent, or Firm—Brumbaugh, Graves, Donohue & Raymond

[57] ABSTRACT

A trephine device for removing anterior epithelial cells from a corneal surface, typically prior to laser excimer reshaping of a portion of the corneal surface, comprises a housing having upper and lower end portions, removal means integral to the housing, and means for activating and deactivating the removal means. The removal means may have at least one cutting surface adapted to conform substantially to the shape of the cornea, with the cutting surface contacted with the cornea at a pressure sufficient to remove the anterior epithelial cells without affecting underlying corneal tissue.

19 Claims, 4 Drawing Sheets

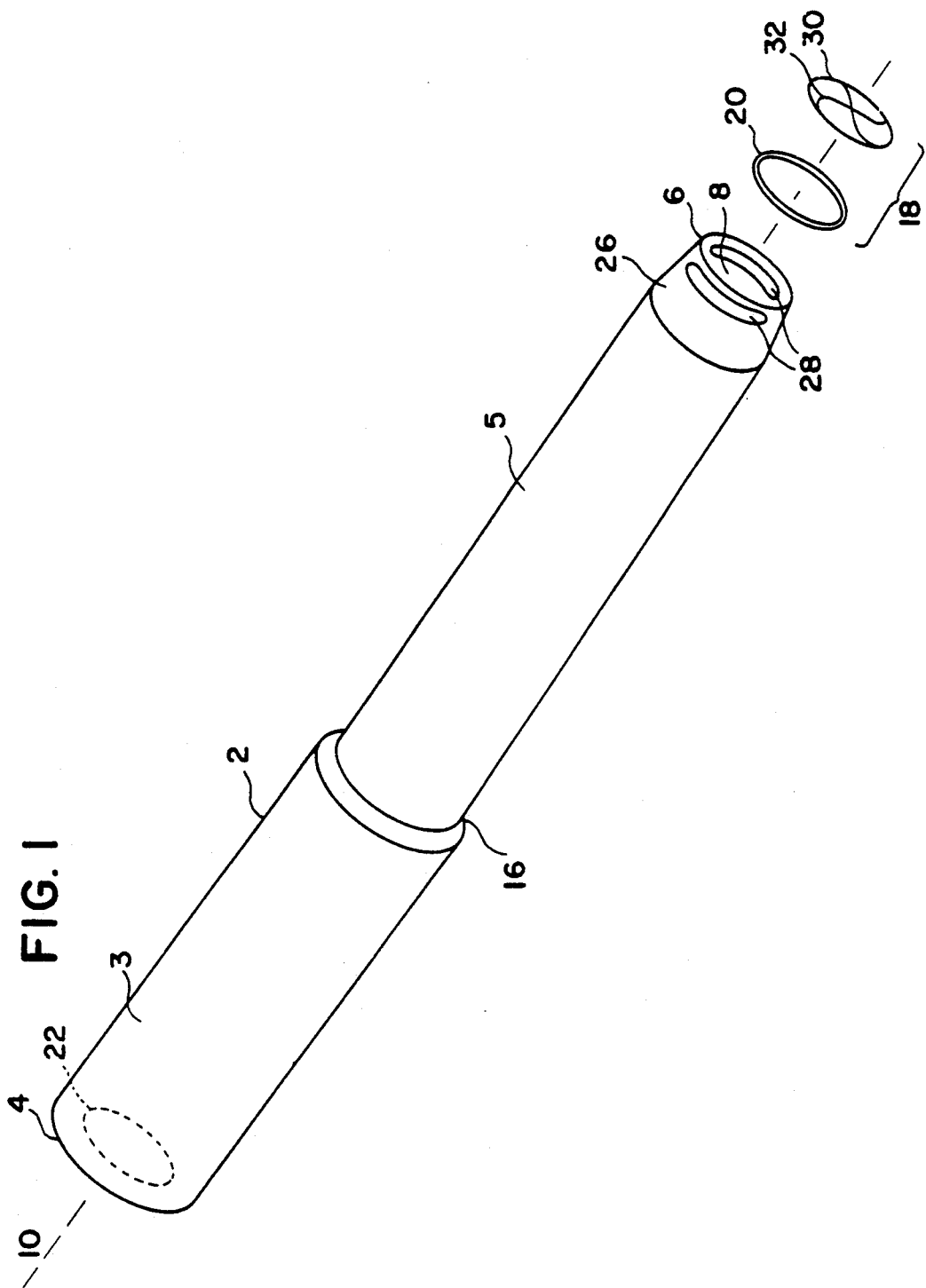

TREPHINE DEVICE FOR REMOVING ANTERIOR EPITHELIAL CELLS FROM CORNEAL SURFACES

BACKGROUND OF THE INVENTION

This invention relates to a trephine device for removing anterior epithelial cells from corneal surfaces. More particularly, this invention relates to a trephine device for removing anterior epithelial cells from corneal surfaces using removal means operated by the surgeon without affecting the underlying corneal tissue, typically prior to the use of an excimer laser to reshape the anterior surface of the cornea.

The use of an excimer laser to reshape the anterior surface of the cornea of the eye to correct refractive defects and other problems is well known to those skilled in the art. It is also well known to those skilled in the art that each pulse of the excimer laser ablates a fixed depth of corneal tissue, with the depth depending on the homogeneity of the tissue and the power output of the laser. For this reason, the superficial layer of epithelial cells or epithelium on the surface of the corneal area to be reshaped must first be uniformly removed since the nucleus and surrounding cortex of the epithelial cells will cause the excimer laser to ablate at a different rate, thereby causing a roughening of the surface of the underlying corneal tissue (i.e. "Bowman's membrane" and corneal stroma) after the epithelium has been ablated. At the present time, the epithelial cells are removed manually by the surgeon using a scraping procedure prior to excimer laser corneal reshaping. However, it is apparent that this procedure requires considerable skill and, if it is not performed perfectly, or nearly perfectly, will result in the uneven removal of the epithelium which will lead to the concomitant uneven ablation of the corneal tissue which is subjected to the excimer laser energy pulse and even the possibility of further detrimental effects to the patient such as corneal scarring and the like. In view of the foregoing, it would clearly be advantageous to employ a device which safely and effectively removes the entire epithelium from the area of the cornea to be reshaped without affecting the underlying corneal tissue prior to excimer laser reshaping of the cornea.

The use of trephine devices for cutting a groove or slit in the cornea or for surgical removal of the cornea is well known to those skilled in the art. For example, U.S. Pat. Nos. 4,763,651 (Kaufman et al.) and 4,750,491 (Kaufman et al.) disclosed a trephine device for cutting a groove in the cornea so that replacement corneal tissue may be tucked into the groove and sewed into place. U.S. Pat. No. 4,336,805 (Smirmaul) discloses a trephine device to remove corneal "buttons" in cornea replacement surgery, as does U.S. Pat. No. 4,190,050 (Bailey). However, a trephine device useful in removing the corneal anterior epithelial cell layer prior to excimer laser reshaping of the cornea, without affecting the underlying corneal tissue, has not previously been disclosed.

It is the object to this invention to provide a trephine device for removing anterior epithelial cells from a corneal surface, without affecting the underlying corneal tissue. It is one feature of this invention that the trephine device employs removal means integral to the housing which may be at least one rotating cutting blade or at least one oscillating cutting blade adapted to conform substantially to the shape of the cornea, or other removal means such as ultrasound activation, to achieve removal of the anterior epithelial cells without affecting the underlying tissue. Since the epithelial cells are relatively gelatinous, it is another feature of this invention that the epithelial cells excised from the area of the cornea to be reshaped by the excimer laser may be transported away from the corneal surface by means such as suction, or in another embodiment, are projected or impelled by the cutting blade or blades through at least one aperture located in the side walls of the trephine device, thereby allowing the epithelial cells to be deposited on the peripheral surface of the cornea where they may thereafter be removed by swabbing or suction techniques.

The present invention is advantageous in that it allows the surgeon uniformly to remove the anterior epithelial cells from the corneal surface without damaging the corneal tissue, e.g. Bowman's layer. By providing a uniform corneal surface to be reshaped by the excimer laser, roughening the underlying corneal tissue due to an uneven ablation of the epithelium is substantially eliminated.

SUMMARY OF THE INVENTION

This invention is directed to a trephine device for removing anterior epithelial cells from a corneal surface, typically prior to excimer laser reshaping of a portion of the anterior surface of the cornea. The device comprises:
(a) a housing having upper and lower end portions;
(b) removal means integral to the housing; and
(c) means for activating and deactivating the removal means.

This invention is advantageous in that it enables the surgeon to remove anterior epithelial cells from an area of the corneal surface prior to excimer laser reshaping of the cornea, with a greatly diminished risk of damaging the underlying corneal tissue. Removal of the epithelium in accordance with the device of this invention provides a smooth underlying corneal tissue surface for excimer laser reshaping.

BRIEF DESCRIPTION OF THE DRAWINGS

FIG. 1 depicts an exploded side view of one embodiment of the device of this invention.

DESCRIPTION OF THE PREFERRED EMBODIMENTS

Figure 2A:
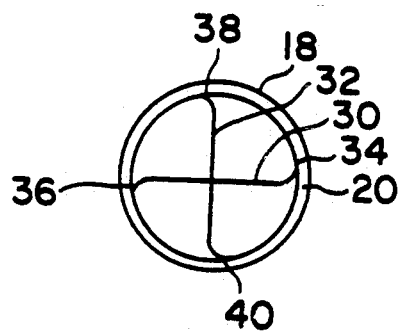
FIGS. 2A-2D depict front views of various embodiments of removal means which may be used in this invention.

The device of this invention comprises a housing, removal means which are attached to the housing, and means for activating and deactivating the removal means to achieve the desired removal of the epithelium of the corneal surface.

The removal means may include any means capable of achieving the desired removal of the epithelium without affecting underlying corneal tissue. More particularly, such means may include application of ultrasonic activation to the corneal surface by means for producing such ultrasonic activation integrated with the housing, or cutting means for removing the epithelium. In one preferred embodiment, cutting means are oscillating cutting means. In a particularly preferred embodiment, the cutting means are rotating cutting means. The cutting means preferably project a fixed distance from the lower end of the housing, and cooperate with the housing in such a manner that the cutting means are applied to the corneal surface at a pressure sufficient to remove the anterior epithelial cells to a predetermined depth thereby avoiding any damage to the underlying corneal tissue.

While various removal means have been disclosed, the present invention is hereafter described in the context of cutting blades. The cutting means typically comprise at least one cutting blade which is a wire of curved shape or capable of assuming a curved shaped in use and adapted to conform substantively to the shape of the cornea. In a preferred embodiment, a plurality of the cutting blades are employed. The cutting blade or blades may be oscillated, rotated, or otherwise caused to move by a variety of mechanical or electrical means well known to those skilled in the art. In one preferred embodiment, rotating cutting means are employed, with each end of the cutting blade wires affixed to a rotatable ring support member, which is engaged and acts in cooperation with the lower end of the housing. The lower end of the housing is in turn engaged to and acts in cooperation with a motor residing in the housing, thereby permitting the lower end of the housing, ring support member and cutting blade or blades to rotate. In another preferred embodiment, the cutting blades have affixed at the center point of intersection of the wires a shaft which is engaged in cooperation with a motor located within the housing for rotating the shaft.

In all embodiments, power may be supplied to the removal means in a manner typically well known to those skilled in the art, which may include use of an external power supply such as alternating or direct current brought to the device by means of suitable circuitry and/or wiring, or a direct current battery either affixed within the housing or exterior to the trephine device. Means for controlling the power supply may include an electrical switch either affixed to the housing or external to the device. In the embodiment wherein the removal means comprise means for subjecting the epithelium to ultrasonic activation, power may be supplied to the means for generating the ultrasonic activation in like manner. In the embodiment wherein cutting means are employed, power may be supplied to a motor for rotating, oscillating or otherwise imparting the necessary movement to the cutting blade or blades. The switch, power supply and removal means may be interconnected to achieve the desired power level or ultrasonic activation (if employed), or the desired rate of rotation or oscillation or other movement, or variable rate of rotation, oscillation or other movement. These may be controlled by means of suitable wiring and circuitry, as is well known to those skilled in the art, as well as means utilizing pressurized gas or fluid.

The housing comprises an upper portion having an upper end, and a lower portion having a lower end. The housing may optionally have an interior portion open along a central axis between the upper and lower ends. In this embodiment, the side walls of the upper and lower portions of the housing and the open interior portion define an upper housing annular open region and lower housing annular open region. In a preferred embodiment, rotating or oscillating means (such as a motor) employed to rotate or oscillate the cutting means are located within one or both of these annular open regions. In a particularly preferred embodiment, a motor is employed to rotate the rotating lower end of the housing, rotatable ring support member and cutting blades, with the motor being located in the annular open region of the upper end of the housing. Accordingly, in this embodiment the open interior portion of the housing may remain unobstructed by the motor and associated linkages and the like necessary to achieve rotation of the cutting blades, thereby enabling the surgeon to have an unrestricted view of the cutting means and corneal surface through the open interior portion when viewed from the upper end of the housing.

The housing may be of any shape, and in one particularly preferred embodiment is cylindrical in shape. In another preferred embodiment, the upper portion of the housing is cylindrical in shape, and the lower portion of the housing is cylindrical in shape with a tapered o conical section to which the rotating ring support member of the cutting blades is affixed and acts in cooperation therewith. In one particularly preferred embodiment, the lower portion of the housing, together with the cutting blade or blades and ring support member may be disengaged from the upper end of the housing, thereby permitting, disposal, replacement, cleaning or sterilization of one or more of the component parts of the lower portion, e.g. the cutting blades and ring support member.

In one preferred embodiment, the surgeon may view the corneal surface from the upper end of the housing through the open interior portion along the central axis of the housing. In this manner, superior control and removal of the epithelium is achieved, as the surgeon is able to View the corneal surface directly and make suitable adjustments during the procedure for removal of the epithelial cells. Additional sighting means to aid the surgeon in viewing the corneal surface during operation of the device may also be employed. Such sighting means will typically be affixed to the upper end of the housing across the open interior portion thereof, and may include additional amplified or unamplified light, lenses, mirrors, filters and the like which may be used to amplify, filter or direct the image of the corneal surface as viewed from the upper end of the housing through the open interior portion thereof. For example, in one embodiment an external light source such as used with an operating microscope may be employed in combination with a magnifying lens affixed to the upper end of the housing across the open interior portion of the housing to enable the surgeon to obtain an illuminated and magnified view of the cutting means as well as the corneal surface. In a preferred embodiment, a suitable light source may be incorporated into the trephine so that the light would be projected downward and thereby effect proper alignment of the device by using the back reflection off the cornea. In the embodiment wherein a motor in combination with a shaft is employed in conjunction with oscillating or rotating cutting means, the sighting means may be positioned to one side of the central axis of the housing, so that the shaft does not block the surgeon's view of the cutting blades and corneal surface. Alternatively, the shaft may be positioned in the center of the housing, and additional sighting means such as a mirror located within the housing acting in cooperation with viewing means such as an eyepiece may be employed to enable the surgeon to view the cutting means and corneal surface.

The housing may additionally comprise pressure-exerting means integral to the housing which exerts pressure upon the cutting blade or blades sufficient to achieve removal of the anterior epithelial cells without affecting underlying corneal tissue. In one embodiment, the pressure exerting means may be a spring-loaded member, with the springs located in an annular region in the upper or lower portion of the housing. In another preferred embodiment, the pressure exerting means is a fluid-containing member, with the pressure-exerting fluid located in the annular region of the upper or lower portion of the housing.

Additionally, pressure sensing means may be interconnected with the pressure-exerting member, with the pressure-sensing means acting cooperatively to activate and deactivate the removal means. For example, in one embodiment the pressure-sensing means may act cooperatively with the pressure-exerting member to activate and deactivate the rotating, oscillating, or otherwise moving means which cause such movement of the cutting blades. In one preferred embodiment, the pressure-sensing means act in cooperation with predetermined first and second pressure signals to cause activation and deactivation of the motor causing rotation of the cutting blades. The pressure sensing means may be of those typically known to those skilled in the art, such as strain gauges, springs and the like, or, where the pressure-exerting member is a fluid-containing member, diaphragm cells, pressure transducers and the like. Pressure switches responsive to pressure-induced input signals may be used to activate and deactivate the motor, to cause rotation and stopping, respectively, of the cutting blade or blades.

The epithelial cells removed from the corneal surface may be transported away from the corneal surface concurrent with or subsequent to use of the device of this invention, by means well known to those skilled in the art, such as by swabbing, suctioning or irrigating solutions. In a particularly preferred embodiment, at least one aperture is located in the side wall of the lower portion of the housing, with the aperture located a fixed distance from the lower end of the housing. The anterior epithelial cells removed from the corneal surface by the removal means (e.g. the rotating or oscillating action of the cutting blades) are projected or impelled by the cutting blade or blades through the aperture or apertures and away from the surgical field, where they may be removed by conventional means.

The trephine devices of the present invention may further be adapted to provide an irrigation means to keep the eye moisturized during the removal of the epithelial cells. For example, a conduit may be formed in the housing one end of which would be connected to a reservoir containing a suitable moisturizing fluid and the other end being open to deliver the fluid to the corneal surface.

The trephine device of this invention will be used in conjunction with medical and surgical procedures well known to those skilled in the art. A typical procedure involves first loosening the patient's corneal epithelium by applying alcohol and/or a local anesthetic (e.g. AMETHOCAINE or PILOCARBINE 1%) to the surface of the cornea. The novel device of the present invention is thereafter placed upon the surface of the cornea and operated as described hereinabove to completely remove the area of epithelium above the corneal surface to be reshaped. Following careful cleaning and drying of the Bowman's membrane until no apparent irregularities of the denuded surface can be detected, reshaping of the corneal surface using the excimer laser may thereafter be accomplished by using procedures well known to those skilled in the art.

The device of this invention will become further apparent from the following detailed description of various preferred embodiments of the invention together with specific references to the accompanying figures.

FIG. 1 depicts an exploded side view of a preferred embodiment of the device of this invention. In this embodiment, housing 2 has an upper portion 3 having an upper end 4, a lower portion 5 having a lower end 6, and an interior portion 8 open along the central axis 10 which runs the length of housing 2 from upper end 4 to lower end 6. The side walls of housing 2 and the open interior portion (not shown) define an upper housing annular region (not shown) and a lower housing annular region (not shown). In this particular embodiment, the lower end 6 may be disengaged from the upper end 4 of the housing, with the line of demarcation between lower portion 5 and upper portion 3 indicated by interface 16. In this embodiment, the removal means consist of cutting means 18 comprising ring support member 20 and a pair of cutting blades 30 and 32 which are positioned directly adjoining and thus projecting a fixed distance from lower end 6. In FIG. 1, the ring support member 20 and cutting blades 30 and 32 are shown detached from lower end 6 of housing 2. In this embodiment, a motor together with associated power source, wiring and the like (not shown) reside in the upper annular region and cause the rotation of lower portion 5 about central axis 10, thereby causing similar rotation of lower end 6 together with cutting means 18.

The surgeon may view the corneal surface (not shown) and cutting blades 30 and 32 in operation through the opening (shown by hidden edge 22) formed in upper end 4 which provides viewing through the open interior portion of the corneal surface and cutting blades 30 and 32. Optionally, additional sighting means such as lenses, mirrors and the like may be affixed within or upon housing 2. For example, in one preferred embodiment, a magnification lens may be affixed atop opening 22, thereby providing the surgeon with a magnified view via the open interior portion of the corneal surface (not shown) and cutting blades 30 and 32.

A pressure-exerting member integral to housing 2 which exerts a pressure upon the cutting blades (not shown) sufficient to achieve removal the anterior epithelial cells without effecting corneal tissue may be located in the upper annular region or lower annular region. This pressure exerting member may be a spring-loaded member, with the spring or springs located in the upper or lower annular region, or may be a fluid-containing member, with the pressure-exerting fluid located in the upper or lower annular region. Optionally, pressure sensing means (not shown) may be interconnected with the pressure-exerting member, with the pressure sensing means acting cooperatively to activate and deactivate the motor causing rotation of lower portion 5, lower end 6 and cutting means 18. In this embodiment, lower portion 5 of housing 2, which terminates at lower end 6, is tapered in shape as shown by tapered section 26, in part to provide easier location and movement of the device prior to and during removal of the anterior epithelial cells.

During operation of the device, the anterior epithelial cells are removed from the corneal surface (not shown) by the rotating action of the cutting blades (not shown) and are thereafter projected or impelled by the cutting blades (not shown) through aperture or apertures 28 located in the side walls of lower portion 5, thereby transporting the removed cells away from the surgically prepared surface of the cornea (not shown). The removed cells may thereafter be removed from the peripheral surface of the cornea (not shown) by conventional means such as suction and the like.

FIG. 2A depicts a front view of cutting means 18 employed in the embodiment of this invention as depicted in FIG. 1. In FIG. 2A, cutting means 18 comprises ring support member 20 and a pair of cutting blades 30 and 32, which are intersecting wires of curved shape adapted to conform to the shape of the corneal surface (not shown). Cutting blades 30 and 32 are affixed to ring support member 20 at their respective ends 34, 36 and 38, 40.

Figure 2B:
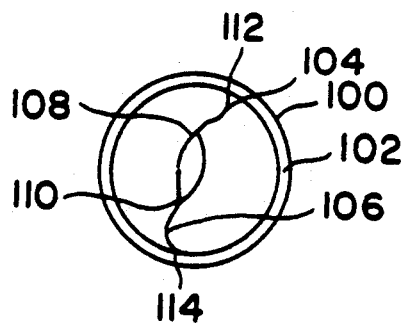
Figure 2C:
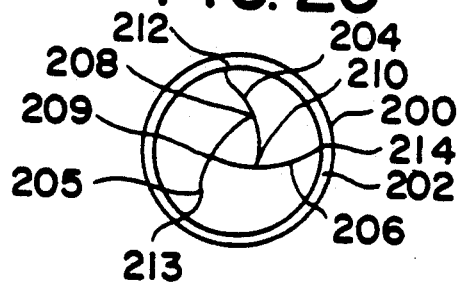
Figure 2D:
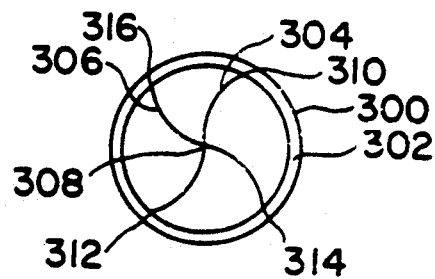

FIGS. 2B, 2C and 2D depict front views of additional embodiments of cutting means which may be employed in this invention. In FIG. 2B, cutting means 100 comprises ring support member 102 and a pair of cutting blades 104 and 106, which are wires of curved shape, as shown, and are interconnected at points 108 and 110, and adapted to conform to the shape of the corneal surface. Cutting blades 104 and 106 are affixed to ring support member 102 at respective ends 112 and 114, as shown. In FIG. 2B, cutting means 200 comprises ring support member 202 and three cutting blades 204, 205 and 206, which are wires of curved shape, as shown, and are adapted to conform to the shape of the corneal surface. Blades 204, 205 and 206 are interconnected at points 208, 209, and 210 as shown, and are affixed to ring support member 202 at respective ends 212, 213 and 214, as shown. In FIG. 2D, cutting means 300 comprises ring support member 302 and a pair of cutting blades 304 and 306, which are wires curved in shape and adapted to conform to the shape of the corneal surface. Blades 304 and 306 are interconnected at point 308, as shown. Blades 304 and 306 are affixed to ring support member 302 at their respective ends 310, 312 and 314, 316 as shown. Other embodiments of cutting means suitable for use in this invention will be apparent to those skilled in the art.

Figure 3:
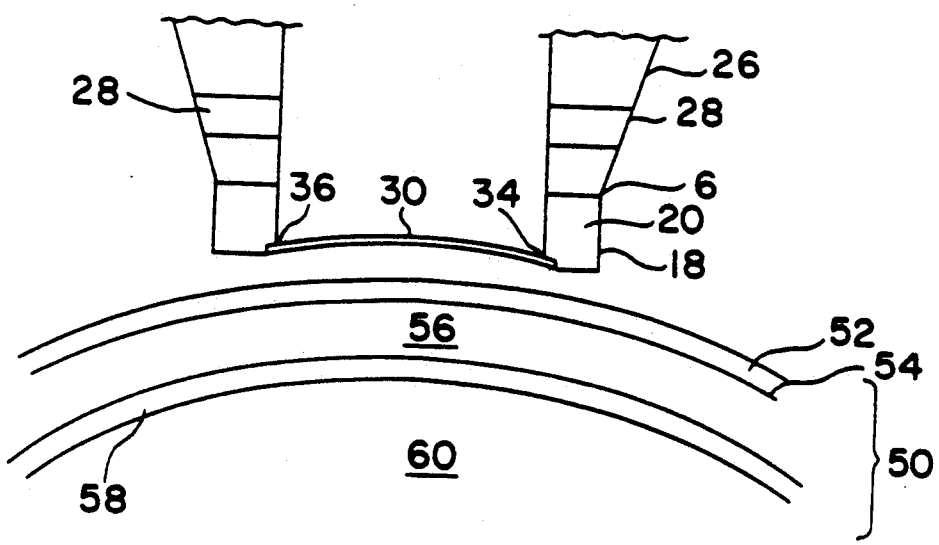
FIG. 3 depicts an expanded cross-sectional view of the lower portion of one embodiment of the device of this invention in conjunction with the anterior portion of the cornea.

FIG. 3 depicts a cross-sectional view of the lower portion of the device of this invention as depicted in FIG. 1, together with a cross-sectional view of the corneal surface to be treated by the device. In FIG. 3, tapered section 26 terminates at lower end 6, and cutting means 18 comprising ring support member 20 and cutting blades 30 and 32 (the latter not shown), with cutting blade 30 affixed to ring support member 20 at ends 34 and 36. Apertures 28 in tapered portion 26 are also shown in cross-section. As depicted in FIG. 3, cutting blade 30 (as well as cutting blade 32 not shown) has a curved shape adapted to the shape of the corneal surface to which the device is to be applied, to ensure that the device sits securely on the corneal surface and properly removes the anterior epithelial cells.

FIG. 3 also depicts the cornea 50 in cross-section, comprising the corneal epithelium 52, a portion of which is to be removed by the trephine device of this invention, the epithelium 52 typically having a cross-sectional thickness in the range of about 30 microns. Beneath the epithelium 52 is Bowman's membrane 54, typically having a thickness in the range of about 15 to 40 microns. Beneath Bowman's membrane are the corneal stroma 56 (which typically has a thickness of about 600 microns) and Descemet's membrane (not shown). Below these lie the corneal endothelium 58 and anterior chamber 60. As previously discussed, when the trephine device is applied to the corneal surface, lower portion 5 (not shown) will be caused to rotate, thereby causing rotation of ring support member 20 and cutting blades 30 and 32 (not shown). The cutting blades will remove a section of the corneal epithelium 52, the section typically having a diameter of about 3 to 7 millimeters depending on the required depth of ablation, to expose the underlying corneal tissue for subsequent laser excimer reshaping thereof to correct refractive defects and the like.

Figure 4:
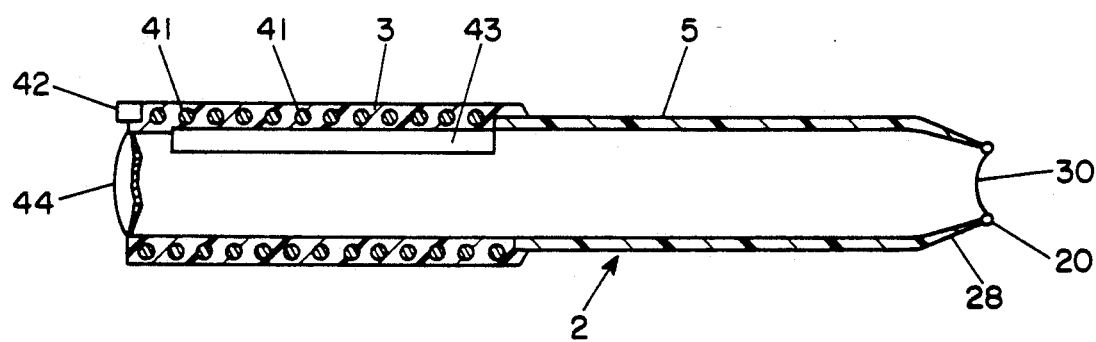
FIG. 4 is a cross section of a device in accordance with the invention.

FIG. 4 is a cross section of the device of the invention. In FIG. 4, the housing 2 is a hollow tube composed of the upper and lower portions 3 and 5. A spring 41 is disposed within the upper portion 3 and exerts pressure on the lower portion 5 and thus on the removal means affixed to the end of the lower portion.

A pressure sensor 42 is disposed in contact with the pressure exerting spring 41. The pressure sensor 42 is connected to a motor, 43 which in turn is coupled to the lower part 5 of the housing 2. The motor is located off of the axis of the open space within the housing in order to leave a central region open for viewing by the surgeon and a magnifying lens 44 is disposed across the open end of the upper portion of the housing.

Although this invention has been illustrated by reference to specific embodiments, it will be apparent to those skilled in the art that Various changes and modifications may be made without departing from the scope of this invention.

I claim:

1. A trephine device for removing anterior epithelial cells from a corneal surface, the device comprising:
   (a) a housing having upper and lower portions;
   (b) cutting means for removing the epithelial cells, said cutting means being integral to the lower portion of the housing and having at least one cutting surface adapted to conform substantially to the shape of the corneal surface, said cutting surface being effective to remove epithelial cells in a substantially circular area corresponding in size to an end of the lower portion of the housing remote from the upper portion of the housing; and
   (c) means for activating and deactivating the cutting means.

2. A device according to claim 1, further comprising means for providing and controlling power to the cutting means.

3. A device according to claim 1, in which the cutting means are oscillating cutting means.

4. A device according to claim 1, in which the cutting means are rotatable cutting means.

5. A device according to claim 4, in which the rotatable cutting means comprise a motor residing in the housing and a shaft having a first end affixed to the motor and a second end affixed to the cutting surface.

6. A device according to claim 4, in which the rotatable cutting means comprise a pair of intersecting wires of curved shape adapted to the shape of the corneal surface and affixed at each end to a rotatable ring support member.

7. A device according to claim 6, in which the rotatable cutting means comprise a motor to drive a rotatable lower end of the housing and a rotatable ring support member.

8. A device according to claim 1, in which the means for activating the cutting means comprise a pressure-exerting member integral to the housing which exerts a pressure upon the cutting surface sufficient to remove the anterior epithelial cells without affecting underlying corneal tissue.

9. A device according to claim 8, in which the pressure exerting member is a spring-loaded member.

10. A device according to claim 8, in which the pressure exerting member is a fluid-containing member.

11. A device according to any one of claims 8-10, in which pressure sensing means are interconnected with the pressure-exerting member, the pressure sensing means acting cooperatively to activate and deactivate the cutting means in correspondence with predetermined first and second pressure signals.

12. A device according to claim 8, further comprising sighting means positioned at the upper end portion of the housing across the open interior portion thereof.

13. A device according to claim 12, in which the sighting means has at least on lens for image magnification of the corneal surface and cutting means.

14. A device according to claim 1, in which the housing has at least one aperture located in a side wall of the housing, said at least one aperture located a fixed distance from the lower end of the housing.

15. A device according to claim 14, in which anterior epithelial cells removed from the cornea by the removal means are projected through at least one aperture and deposited on the peripheral surface of the cornea.

16. A trephine device for removing anterior epithelial cells from a corneal surface, the device comprises:
  (a) a housing having upper and lower portions;
  (b) removal means for removing the epithelial cells integral to the lower portion of the housing; and
  (c) means for activating and deactivating the removal means, wherein the housing as an interior portion open along a central axis between the upper and lower housings, the open portion permitting viewing therethrough of the removal means and the corneal surface.

17. A device according to claim 16, wherein the removal means is a cutting means having at least one cutting surface adapted to conform substantially to the shape of the corneal surface.

18. A device according to claim 17, in which the means for activating the removal means comprises a pressure exerting member integral to the housing which exerts a pressure upon the cutting surface sufficient to remove the anterior epithelial cells without affecting the underlying corneal tissue.

19. A device according to claim 17, wherein the cutting means is a rotatable cutting means.

* * * * *

UNITED STATES PATENT AND TRADEMARK OFFICE
CERTIFICATE OF CORRECTION

PATENT NO. : 5,269,795

DATED : December 14, 1993

INVENTOR(S) : Eric J. Arnott

It is certified that error appears in the above-identified patent and that said Letters Patent is hereby corrected as shown below:

Col. 4, line 37, "View" should read --view--;

Col. 6, line 51, "removal" should read --removal of--;

Col. 6, line 52, "effecting" should read --affecting--;

Col. 8, line 33, "Various" should read --various--;

Col. 9, line 23, "on lens" should read --one lens--;

Col. 10, line 6, "comprises" should read --comprising--;

Col. 10, line 11, "housing as" should read --housing has--.

Signed and Sealed this

Ninth Day of August, 1994

Attest:

BRUCE LEHMAN

Attesting Officer

Commissioner of Patents and Trademarks